United States Patent
Ward et al.

(10) Patent No.: US 7,888,275 B2
(45) Date of Patent: Feb. 15, 2011

(54) POROUS COMPOSITE MATERIALS COMPRISING A PLURALITY OF BONDED FIBER COMPONENT STRUCTURES

(75) Inventors: Bennett C. Ward, Midlothian, VA (US); Wolfgang Broosch, Schwarzenbek (DE); Bernhard E. Kutscha, Reinbek (DE); Dirk H. Kemper, Wohltorf (DE)

(73) Assignee: Filtrona Porous Technologies Corp., Colonial Heights, VA (US)

( * ) Notice: Subject to any disclaimer, the term of this patent is extended or adjusted under 35 U.S.C. 154(b) by 1055 days.

(21) Appl. No.: 11/333,499

(22) Filed: Jan. 17, 2006

(65) Prior Publication Data

US 2006/0163152 A1    Jul. 27, 2006

Related U.S. Application Data

(60) Provisional application No. 60/645,680, filed on Jan. 21, 2005, provisional application No. 60/748,568, filed on Dec. 8, 2005.

(51) Int. Cl.
*D04H 1/00* (2006.01)
*B01D 24/00* (2006.01)
*B01D 47/16* (2006.01)

(52) U.S. Cl. .................. 442/353; 210/508; 210/505; 261/99; 261/104; 261/107; 428/373

(58) Field of Classification Search ............. 442/327, 442/347, 329, 340, 345, 409, 382, 353; 428/375, 428/373, 325; 210/505, 508; 347/86
See application file for complete search history.

(56) References Cited

U.S. PATENT DOCUMENTS

| | | | |
|---|---|---|---|
| 2,277,377 A | 4/1942 | Warner | |
| 3,533,416 A | 10/1970 | Berger et al. | |
| 3,595,245 A | 7/1971 | Buntin et al. | |
| 3,599,646 A | 8/1971 | Berger et al. | |
| 3,615,995 A | 10/1971 | Buntin et al. | |
| 3,637,447 A | 1/1972 | Berger et al. | |
| 3,703,429 A | 11/1972 | Berger et al. | |
| 3,801,400 A | 4/1974 | Vogt et al. | |
| 3,972,759 A | 8/1976 | Buntin | |
| 4,563,392 A | 1/1986 | Harpell et al. | |
| 4,739,928 A | 4/1988 | O'Neil | |
| 4,830,904 A | 5/1989 | Gessner et al. | |
| 5,143,779 A | 9/1992 | Newkirk et al. | |
| 5,277,974 A | 1/1994 | Kubo et al. | |
| 5,306,534 A | 4/1994 | Bosses | |
| 5,405,682 A | 4/1995 | Shawyer et al. | |
| 5,418,045 A | 5/1995 | Pike et al. | |
| 5,425,987 A | 6/1995 | Shawver et al. | |
| 5,437,899 A | 8/1995 | Quigley | |

(Continued)

FOREIGN PATENT DOCUMENTS

WO    WO 2005/094245 A2    10/2005

*Primary Examiner*—Angela Ortiz
*Assistant Examiner*—Altrev C Sykes
(74) *Attorney, Agent, or Firm*—Hunton & Williams

(57) ABSTRACT

An integrally formed multi-component structure is disclosed, the multi-component structure comprising a plurality of components, at least one of which is a three-dimensional bonded fiber fluid transmissive component comprised of a plurality of polymeric fibers bonded to each other at spaced apart contact points, the fibers collectively defining tortuous fluid flow paths, and wherein each component has an interface with at least one other component.

41 Claims, 9 Drawing Sheets

U.S. PATENT DOCUMENTS

| | | |
|---|---|---|
| 5,456,982 A | 10/1995 | Hansen et al. |
| 5,534,340 A | 7/1996 | Gupta et al. |
| 5,545,464 A | 8/1996 | Stokes |
| 5,607,766 A | 3/1997 | Berger |
| 5,620,641 A | 4/1997 | Berger |
| 5,633,082 A | 5/1997 | Berger |
| 5,657,065 A | 8/1997 | Lin |
| 5,780,155 A | 7/1998 | Ishizawa et al. |
| 5,798,305 A | 8/1998 | Horiuchi |
| 5,804,517 A | 9/1998 | Ishii et al. |
| 5,935,883 A | 8/1999 | Pike |
| 6,001,752 A | 12/1999 | Ishizawa et al. |
| 6,103,181 A | 8/2000 | Berger |
| 6,174,603 B1 | 1/2001 | Berger |
| 6,225,243 B1 | 5/2001 | Austin |
| 6,234,618 B1 | 5/2001 | Yamamoto et al. |
| 6,270,206 B1 | 8/2001 | Shimizu et al. |
| 6,325,498 B1 | 12/2001 | Higuma et al. |
| 6,330,883 B1 | 12/2001 | Berger |
| 6,334,674 B1 | 1/2002 | Ono et al. |
| 6,382,786 B2 | 5/2002 | Iwanaga et al. |
| 6,394,591 B1 | 5/2002 | Higuma et al. |
| 6,412,932 B1 | 7/2002 | Higuma et al. |
| 6,417,121 B1 | 7/2002 | Newkirk et al. |
| 6,417,122 B1 | 7/2002 | Newkirk et al. |
| 6,419,350 B1 | 7/2002 | Abe et al. |
| 6,420,285 B1 | 7/2002 | Newkirk et al. |
| 6,482,895 B2 | 11/2002 | Maugans et al. |
| 6,485,136 B1 | 11/2002 | Shimizu et al. |
| 6,506,698 B1 | 1/2003 | Quantrille et al. |
| 6,518,208 B2 | 2/2003 | Terakawa |
| 6,578,957 B2 | 6/2003 | Higuma et al. |
| 6,632,504 B1 | 10/2003 | Gillespie et al. |
| 6,634,739 B2 | 10/2003 | Hayashi et al. |
| 6,692,115 B2 | 2/2004 | Sanada et al. |
| 6,696,373 B2 | 2/2004 | Kinn et al. |
| 6,698,871 B1 | 3/2004 | Hayashi et al. |
| 6,723,669 B1 | 4/2004 | Clark et al. |
| 6,796,645 B2 | 9/2004 | Hayashi et al. |
| 6,797,226 B2 | 9/2004 | Annable |
| 6,809,047 B2 | 10/2004 | Lebold et al. |
| 6,815,381 B1 | 11/2004 | Yamamoto et al. |
| 6,827,431 B2 | 12/2004 | Kitabatake et al. |
| 6,840,692 B2 | 1/2005 | Ward et al. |
| 6,958,103 B2 | 10/2005 | Anderson et al. |
| 7,018,031 B2 | 3/2006 | Ward et al. |
| 7,045,211 B2 | 5/2006 | Fairbanks et al. |
| 7,290,668 B2 * | 11/2007 | Ward et al. .................. 210/508 |
| 2001/0009432 A1 | 7/2001 | Olsen et al. |
| 2002/0016120 A1 | 2/2002 | Nagano et al. |
| 2002/0021340 A1 | 2/2002 | Olsen et al. |
| 2002/0113853 A1 | 8/2002 | Hattori et al. |
| 2003/0043241 A1 | 3/2003 | Hattori et al. |
| 2003/0114066 A1 | 6/2003 | Clark et al. |
| 2004/0041285 A1 | 3/2004 | Xiang et al. |
| 2004/0132376 A1 | 7/2004 | Haworth |
| 2005/0212878 A1 * | 9/2005 | Studer et al. .................. 347/86 |
| 2006/0084342 A1 | 4/2006 | Austin et al. |

* cited by examiner

US 7,888,275 B2

POROUS COMPOSITE MATERIALS COMPRISING A PLURALITY OF BONDED FIBER COMPONENT STRUCTURES

This application claims priority to Provisional Application Ser. No. 60/645,680, filed on Jan. 21, 2005, and Provisional Application Ser. No. 60/748,568, filed on Dec. 8, 2005, each of which is incorporated herein by reference.

BACKGROUND OF THE INVENTION

The invention relates generally to the field of bonded polymeric fiber structures and, more particularly, to multi-component structures comprising a plurality of components, at least one of which is a three dimensional bonded fiber structure. Specifically, two or more components may be integrally formed into a single, substantially self-sustaining, three dimensional structure, in which at least one component is a three dimensional bonded fiber structure. This resultant structure may exhibit, in different components, different structural characteristics and resulting properties.

A fiber component and material used in a particular bonded fiber component may be tailored to specific applications. In particular, specific fiber types may be selected to provide a particular set of fluid manipulation properties and/or facilitate processing. For example, some fiber types may provide a higher surface energy that would facilitate wicking of a fluid. Other fiber types may provide bonding advantages. In some polymeric fiber components, a plurality of different fiber types may be used to provide a particular combination of characteristics.

The inclusion of a non-fibrous component in the integrally formed multi-component structure may provide additional benefits. For example, a permeable or impervious membrane may be included to provide particular fluid treatment properties. Similarly, non fibrous components may be included to provide additional structural, mechanical, filtering, or any other properties.

Bonded polymeric fiber components and structures have demonstrated distinct advantages for fluid storage and fluid manipulation applications, since such bonded fiber structures have been shown to take up ink of various formulations and controllably release it. A typical use for these components and structures may include use as nibs for writing instruments, ink reservoirs, wicks for a wide variety of devices and applications, depth filters, and other applications where the surface area and porosity characteristics of such components or structures are advantageous.

Additionally, fiber components and structures may find use in diverse medical applications, for example, to transport a bodily fluid by capillary action to a test site or diagnostic device. Other applications of fibrous products are as absorption reservoirs, products adapted to take up and simply hold liquid as in a diaper or incontinence pad. Still other applications of bonded fiber components and structures may be high temperature filtration elements. Characteristics beneficial to the application as a high temperature filtration element include a relatively high melting temperature, and the definition of a tortuous interstitial path effective for capturing of fine particulate matter when a gas or liquid is passed through the fiber filter.

As described in U.S. Pat. Nos. 5,607,766, 5,620,641, 5,633,082, 6,103,181, 6,330,883, and 6,840,692, each of which is incorporated herein by reference in its entirety, there are many forms of and uses for bonded fiber components and structures, as well as many methods of manufacture. In general, such bonded fiber components and structures are formed from webs of thermoplastic fibrous material comprising an interconnecting network of highly dispersed continuous fibers bonded to each other at points of contact. These webs can then be formed into substantially self-sustaining, three-dimensional porous components and structures. These components or structures may provide high surface areas and porosity, and may be formed in a variety of sizes and shapes.

SUMMARY OF THE INVENTION

Aspects of the invention include an integrally formed multi-component structure comprising a plurality of components, at least one of which is a three-dimensional bonded fiber fluid transmissive component comprised of a plurality of polymeric fibers bonded to each other at spaced apart contact points, the fibers collectively defining tortuous fluid flow paths, and wherein each component has an interface with at least one other component.

It is to be understood that both the foregoing general description and the following detailed description are exemplary and explanatory only, and are not restrictive of the invention as claimed. The accompanying drawings, which are incorporated herein by reference, and which constitute a part of the specification, illustrate certain embodiments of the invention and, together with the detailed description, serve to explain the principles of the invention.

BRIEF DESCRIPTION OF THE DRAWINGS

In order to assist in the understanding of the invention, reference will now be made to the appended drawings, in which like reference characters refer to like elements. The drawings are exemplary only, and should not be construed as limiting the invention.

DETAILED DESCRIPTION OF THE INVENTION

Figure 1:
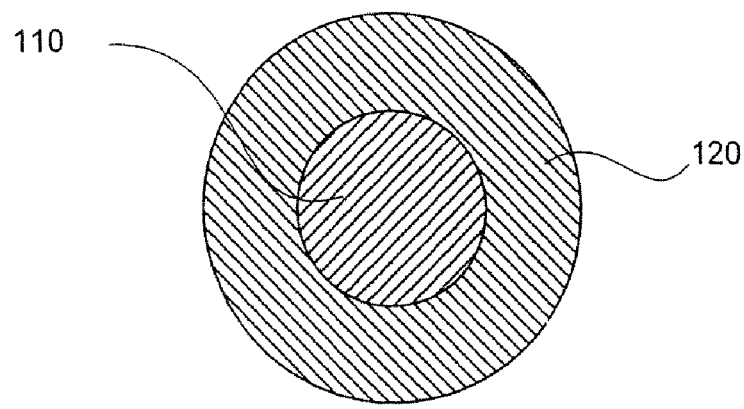
FIG. 1 is a cross-sectional view of a two-component three dimensional bonded fiber structure in accordance with some embodiments of the invention.
Figure 2:
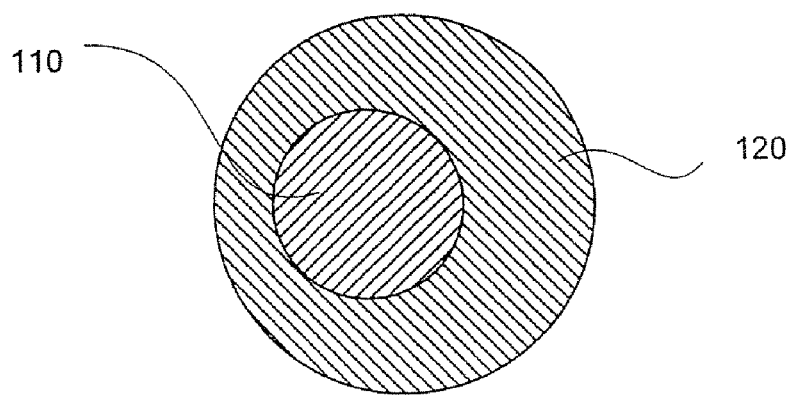
FIG. 2 is a cross-sectional view of another two-component three dimensional bonded fiber structure in accordance with some embodiments of the invention.

Reference will now be made in detail to embodiments of the invention, examples of which are illustrated in the accompanying drawings.

The term "bicomponent fiber" as used herein refers to the use of two polymers of different chemical nature placed in discrete portions of a fiber structure. While other forms of bicomponent fibers are possible, the more common techniques produce either "side-by-side" or "sheath-core" relationships between the two polymers. For example, bicomponent fibers comprising a core of one polymer and a coating or sheath of a different polymer are particularly desirable for many applications since the core material may be relatively inexpensive, providing the fiber with bulk and strength, while a relatively thin coating of a more expensive or less robust sheath material may provide the fiber with unique properties.

The term "bicomponent fiber" is not to be confused with the term "bicomponent structure," which as used herein refers to an integrally formed three dimensional structure comprised of two distinct components. Each component may or may not be made from "bicomponent fibers."

The term "component" as used herein refers to a distinct portion of a multi-component structure that is uniform in material and properties, and may also be referred to as a "substructure."

The term "fluid" as used herein refers to a substance whose molecules move freely past one another, including but not limited to a liquid or gas. The term "fluid" as used herein may also be multi-phase, and may include particulate matter suspended in a liquid or gas.

When multiple fiber materials are used in manufacturing techniques commonly known in the art, the overall resultant structure is substantially isotropic; that is, its structural characteristics and resulting properties (e.g., density, porosity, surface area, surface energy, etc.) are substantially uniform throughout the structure. However, a fiber structure may be comprised of two or more distinct components. By varying material, or at times the fiber types and/or characteristics in each component, an anisotropic multi-component structure may be created. The components may differ in various characteristics, including but not limited to, material, density, porosity, surface area, surface energy, finish treatments, particulate loading, etc.

The invention provides for multi-component structures that are comprised of two or more distinct components, where at least one component is a three dimensional bonded fiber fluid transmissive component. The distinct components may possess different characteristics and/or properties. For example, in a typical embodiment, a multi-component structure may be comprised of a three dimensional bonded fibrous component and a non-fibrous component. The three dimensional bonded fibrous component may be comprised of an interconnecting network of highly dispersed fibers bonded to each other at spaced points of contact. The non-fibrous component may be, but is not limited to, permeable or impervious membranes, solid components (formed of, e.g. plastic, metal, composites), paper, cloth, or any other material.

Similarly, the invention provides for a multi-component structure that may have a first component formed of a first thermoplastic fibrous material and a second component formed of a second thermoplastic fibrous material. Each material may comprise an interconnecting network of highly dispersed fibers bonded to each other at points of contact. These first and second three dimensional bonded fiber components may be integrally formed to form an overall multi-component three dimensional bonded fiber structure. In some embodiments, the first and second components may be coextensive elongate components and the resulting composite structure may be an elongate self-sustaining rod. The cross-section of this resultant rod may exhibit a first area established by the first component and a second area established by the second component.

An interface may exist between the two or more components. If the interface is between two or more fibrous components, a portion of the fibers from one component may be bonded to fibers of at least one other component. The degree of fiber intermingling between components may be dependent upon the manufacturing process used to manufacture the overall integrally formed three dimensional multi-component structure. The interface between two or more components wherein one of the components is not a fibrous component may or may not have any fiber bonding. This type of interface may be held in place by a mechanical connection, interference fit, friction, or by some fiber bonding.

Multi-component structures having multiple fibrous components may have many benefits. For example, structures having at least two component three dimensional bonded fiber components with different densities and/or porosities can be used to accommodate different fluid flow characteristics and flow speeds. An application could be as a combination of hydrophobic and hydrophilic structure components. Such a structure may be beneficial in an ink cartridge. The hydrophobic layer could be used to keep ink away from air vents (preventing leakage) and also keep the ink out of unproductive corners of a reservoir, which would reduce the amount of residual ink in the reservoir upon exhaustion. Using distinct hydrophobic and hydrophilic, or oleophobic and oleophilic, components in an air freshener can similarly be used to separately wick two different fluids; for example, a water-based fluid and an alcohol or hydrocarbon-based fluid. This may enable an even evaporation rate of two different phases within an air freshener container. For example, the air freshener could contain a fragrance dissolved in an aqueous phase, and a different fragrance dissolved in a hydrocarbon phase. The air freshener wick would be formed as a two-component composite structure, each component having different characteristics tailored to allow an even evaporation rate of the two fragrances. The two components could also be formed in different colors to illustrate that the two different liquids are evaporating and to indicate whether the phases are still active.

Some embodiments of the invention may provide a multi-component structure in which one or more components are formed from bonded fiber structures and one or more components are formed from other materials. The inclusion of non-fibrous components in integrally formed multi-component structure may provide additional benefits. For example, a permeable or impervious membrane may be included to provide particular fluid treatment properties. Similarly, non fibrous components may be included to provide additional structural, mechanical, filtering, or any other properties.

A particular multi-component structure according to an embodiment of the invention may be formed as a two-component structure where at least one component exhibits air deodorizing characteristics. In a particular embodiment of the invention, at least one component is a bonded, porous and air-permeable fiber element and a second component may be fibrous or non-fibrous. The second component may exhibit air deodorizing characteristics. The second component may be, for example, carbon impregnated paper. However, the air deodorizing component may comprise any suitable material and may be formed as a bonded fiber structure.

In a multi-component air-deodorizer as described above, the components may be arranged in any manner, including but not limited to side-by-side, layered, or with one component nested within another. In a particular embodiment of the invention, the component that exhibits air-deodorizing characteristics may be nested within a bonded fiber component. The bonded fiber component may be air permeable, thereby allowing air to flow to and from the air-deodorizing component. In some embodiments of the invention, the bonded fiber component may provide structural support for the overall multi-component structure. Additionally, the exterior bonded fiber component may be an optically pleasing color, such as white, and may conceal a less optically pleasing nested component.

Various prior art techniques are known for the production of products from polymeric fibers. The polymeric fibers themselves may be produced by a number of common techniques, oftentimes dictated by the nature of the polymer and/or the desired properties and applications for the resultant fibers. Among such techniques are conventional melt spinning processes, wherein a molten polymer is pumped under pressure to a spinning head and extruded from spinerette orifices into a multiplicity of continuous fibers. However, melt spinning is typically only available for polymers having a melting point temperature less than its decomposition temperature, such as nylon, polypropylene and the like. Other polymers, such as the acrylics, generally cannot be melted without blackening and decomposing. Melt spinning techniques are commonly employed to make both mono-component and bi or multi-component fibers. In addition, some polymers can be dissolved in a suitable solvent (e.g., cellulose acetate in acetone) of typically 25% polymer and 75% solvent. In a wet spinning process, the solution is pumped at room temperature through the spinerette which is submerged in a bath of a liquid non-solvent in which the non-solvent serves to coagulate the polymer to form polymeric fibers. It is also possible to dry spin the fibers into hot air (or other hot gas), rather than a liquid bath, to evaporate the solvent and form a solid fiber strand. These and other common spinning techniques are well known in the art.

After spinning, the fibers are typically attenuated. Attenuation can occur by drawing the fibers from the spinning device at a speed faster than their extrusion speed, thereby producing fibers which are finer, i.e. smaller in diameter. This attenuation may be accomplished by taking the fibers up on rolls rotating at a speed faster than the rate of extrusion. Attenuation my also be accomplished by drawing the fibers utilizing draw rolls operating at different speeds. Depending on the nature of the polymer, drawing the fibers in this manner may orient the polymer chains, thus improving the physical properties of the fiber. Melt-spinning, as described above and as known in the art, is a typical method of making both mono-component and bicomponent fibers.

Mono-component, bicomponent, and multi-component fibers may be formed by melt blowing. Briefly, melt-blowing involves the use of a high speed, typically high temperature gas stream at the exit of a fiber extrusion die to attenuate or draw out the fibers while they are in their molten state. See, for example, U.S. Pat. Nos. 3,595,245, 3,615,995 and 3,972,759 (the '245, the '995 and '759 patents, respectively), the subject matters of which are incorporated herein in their entirety by reference, for a comprehensive discussion of the melt blowing processing. Melt blowing of fibrous materials can produce a web or roving wherein the fibers have, on the average, a diameter of about 12 microns or less, down to 5 and even 1 micron. Such fine melt blown fibers may have significant advantages in particular applications. For example, when used in the production of ink reservoirs, the small diameter fibers have demonstrated a higher surface area and an increased holding capacity as compared to the use of larger diameter fibers made by other techniques. These fibers may also provide enhanced filtration efficiency when used in the production of filter elements, due to increased fiber surface area for the same weight of polymer. These fine fibers are commonly collected as an entangled web on a continuously moving surface, such as a conveyor belt or a drum surface, for subsequent processing.

Fibrous products often require, or are enhanced by, the incorporation of an additive in the fibrous web during manufacture. The addition of selected surfactants or other chemical agents in a particular concentration to a fibrous media to be used as an ink reservoir for marking and writing instruments or ink jet printer reservoirs may modify the surface characteristics of the fibers to enhance absorptiveness and/or compatibility with particular ink formulations. Similarly, wicking materials used in various medical applications may be treated with solutions of active ingredients, such as monoclonal antibodies, to interact with materials passed therethrough.

In some instances, an additive can simply be added to the polymer melt prior to extrusion. However, for many applications this approach either is impossible or inefficient. Alternatively, it is possible to topically apply liquid surface treatments to the fibrous material during manufacture, such as by soaking the fibrous materials in highly diluted solutions of the additive in an attempt to insure that adequate additive material is incorporated throughout the fibrous structure.

However, this process generally results in a fibrous structure with isotropic properties. Methods that involve treating only sections of the fibrous structure may create anisotropic properties to exist, but difficulties arise in manufacturing components with two or more component structures or substructures, each with different characteristics. This difficulty is increased when the two or more component structures or substructures are not symmetric.

Figure 3:
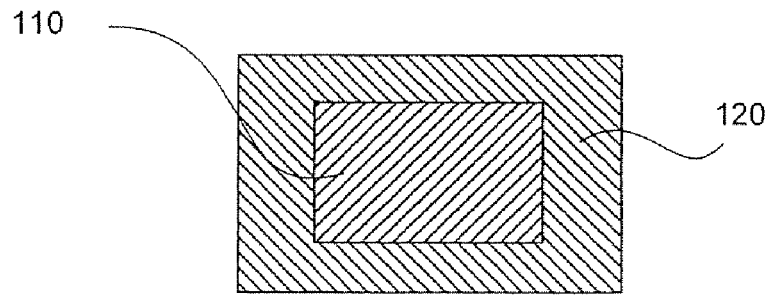
FIG. 3 is a cross-sectional view of another two-component three dimensional bonded fiber structure in accordance with some embodiments of the invention.
Figure 4:
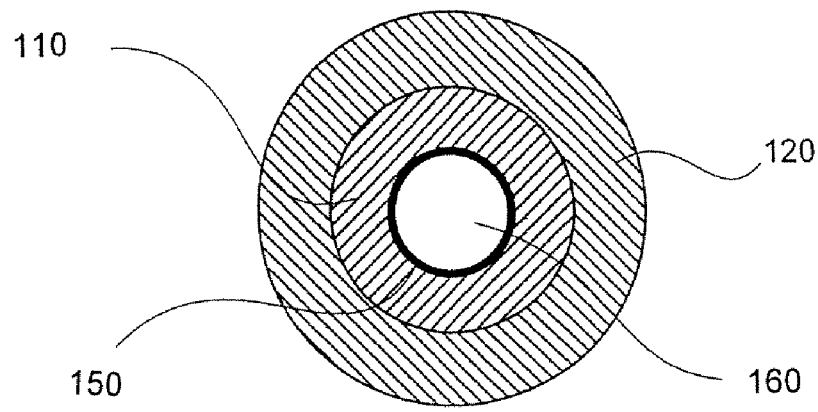
FIG. 4 is a cross-sectional view of a two-component three dimensional bonded fiber structure, including a void bounded by a membrane, in accordance with some embodiments of the invention.
Figure 5:
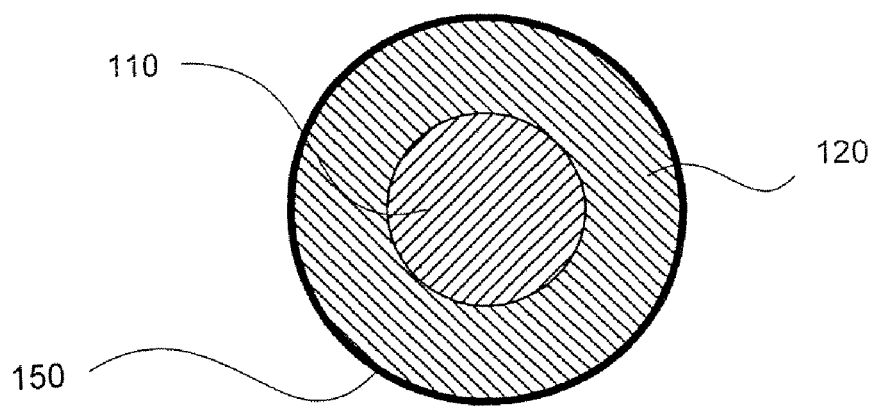
FIG. 5 is a cross-sectional view of a two-component three dimensional bonded fiber structure where the outermost component is bounded by a membrane, in accordance with some embodiments of the invention.
Figure 6:
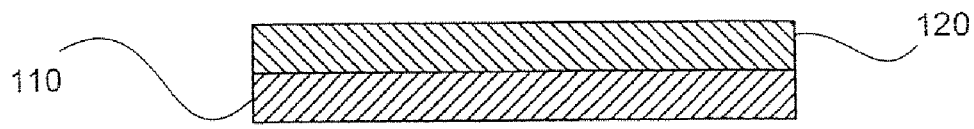
FIG. 6 is a cross-sectional view of a stratified two-component three dimensional bonded fiber structure in accordance with some embodiments of the invention.
Figure 7:
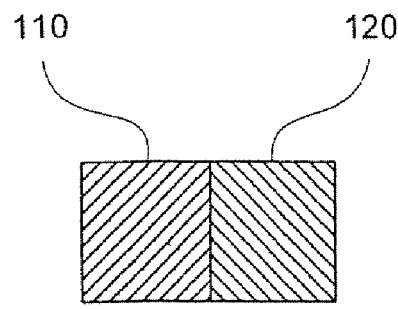
FIG. 7 is a cross-sectional view of another stratified two-component three dimensional bonded fiber structure in accordance with some embodiments of the invention.
Figure 8:
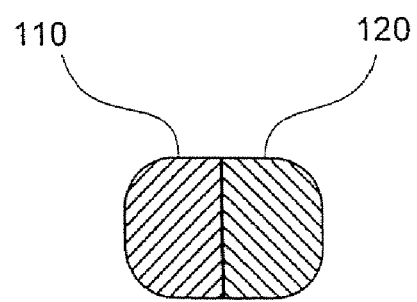
FIG. 8 is a cross-sectional view of another stratified two-component three dimensional bonded fiber structure in accordance with some embodiments of the invention.
Figure 9:
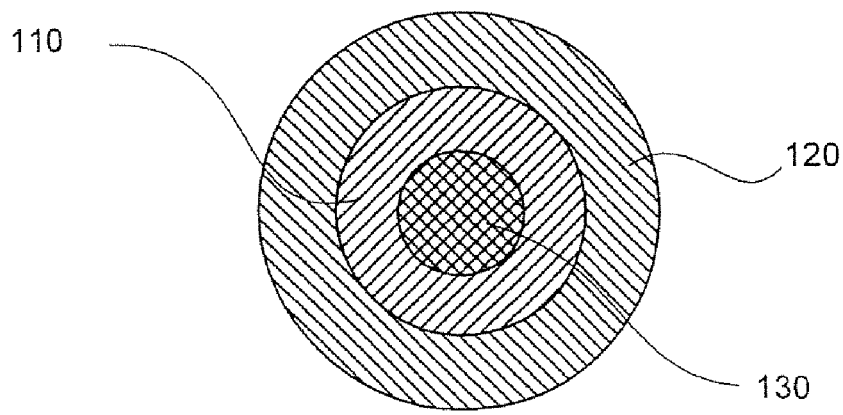
FIG. 9 is a cross-sectional view of a nested three-component three dimensional bonded fiber structure in accordance with some embodiments of the invention.
Figure 10:
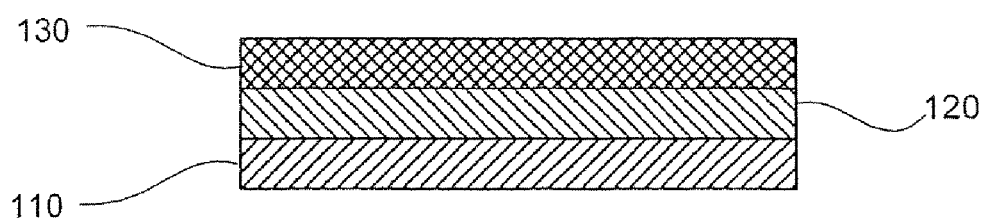
FIG. 10 is a cross-sectional view of a stratified three-component three dimensional bonded fiber structure in accordance with some embodiments of the invention.
Figure 11:
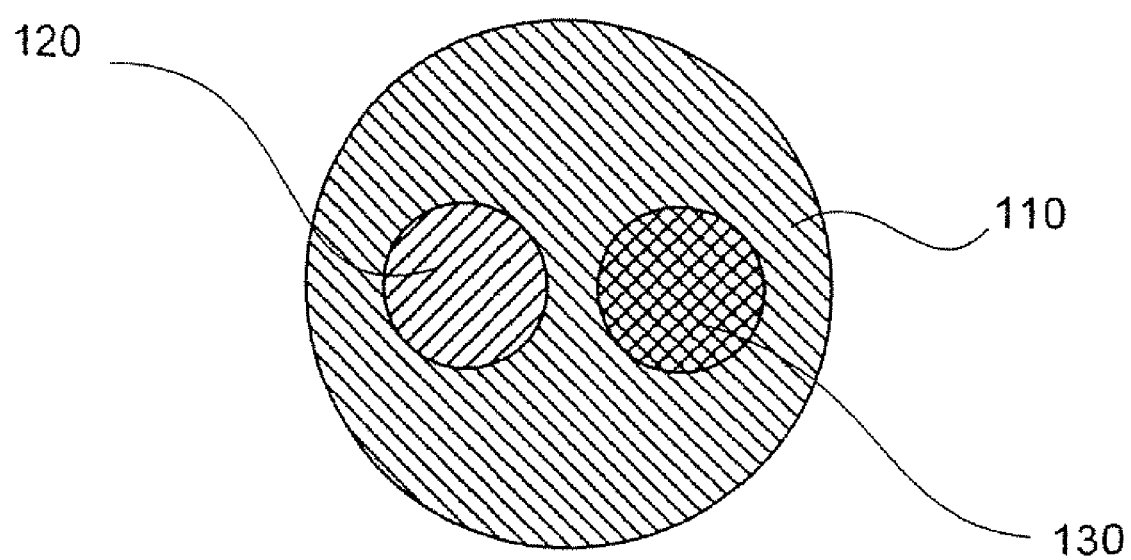
FIG. 11 is a cross-sectional view of another nested three-component three dimensional bonded fiber structure in accordance with some embodiments of the invention.

FIGS. 1-11 illustrate various configurations of multi-component structures according to the invention. Each figure shows the cross-section of an overall structure formed from a first component 110 and a second component 120. FIGS. 1, 2, 4, 5, 9 and 11 are examples of structures in which one or both of the first and second components 110, 120 are circular cylinders with one of the components nested within the other. FIGS. 3, 6, 7, 8, and 10 are examples in which the first and second components 110, 120 are prisms with rectangular cross-sections. FIG. 3 shows the first component 110 nested within the second component 120. FIGS. 6 and 10 illustrate a stratified, or laminate structure, and FIGS. 7 and 8 illustrate a tandem, or side-by-side configuration.

Figure 12:
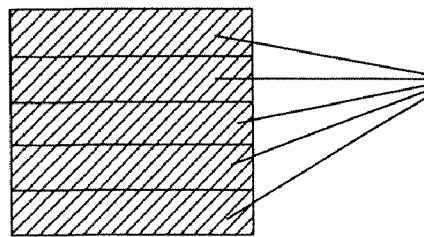
FIG. 12 is a cross-sectional view of a multi-component, isotropic three dimensional bonded fiber structure in accordance with some embodiments of the invention.
Figure 13:
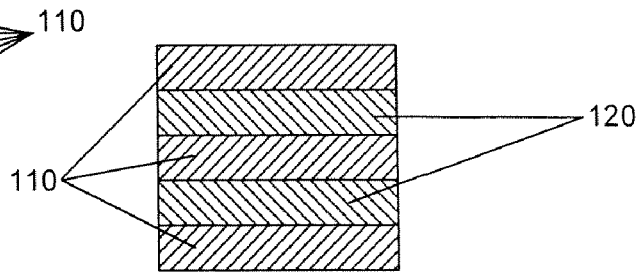
FIG. 13 is a cross-sectional view of a multi-component, anisotropic three dimensional bonded fiber structure in accordance with some embodiments of the invention.
Figure 14:
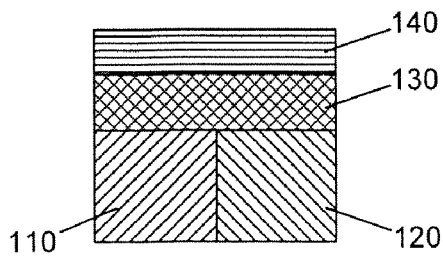
FIG. 14 is a cross-sectional view of a multi-component anisotropic three dimensional bonded fiber structure in accordance with some embodiments of the invention.
Figure 15:
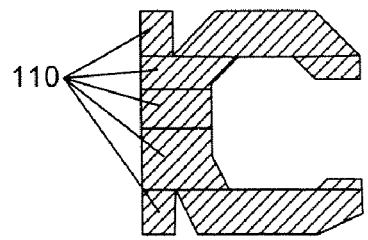
FIG. 15 is a cross-sectional view of an asymmetric multi-component, isotropic three dimensional bonded fiber structure in accordance with some embodiments of the invention.
Figure 16:
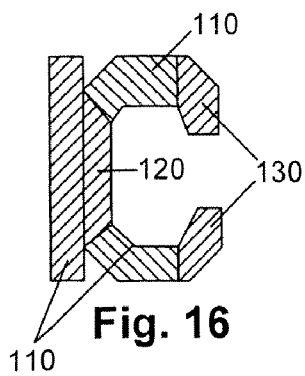
FIG. 16 is a cross-sectional view of an asymmetric multi-component, anisotropic three dimensional bonded fiber structure in accordance with some embodiments of the invention.

FIGS. 12 and 15 illustrate integrally formed multi-component structures where each component 110 is the same, thereby forming a substantially isotropic multi-component structure. FIGS. 13, 14, and 16 illustrate integrally formed multi-component structures with at least two types of components, thereby forming anisotropic multi-component structures. FIG. 13 illustrates an integrally formed multi-component structure with two components similar to a laminate, where the first component 110 and the second component 120 alternate. FIG. 14 illustrates an integrally formed multi-component structure with four components. The structure depicted in FIG. 14 may have various components of differing characteristics located at various places in the structure. FIG. 16 illustrates an integrally formed multi-component structure with three components located at various places in the structure.

The selection of the component properties and placement in FIGS. 14 and 16 may be based upon the desired characteristics of the final product. For example, FIG. 16 depicts the cross-section of a "C" shaped structure that may be used to "snap" or "clamp" onto another device. A mechanical fit such as this "snap" or "clamp" may be dependent upon the flexibility of portions of the "C" shaped structure. However, other portions may be desired to be rigid, absorbent, or some other characteristic.

Therefore, a cross-section as shown in FIG. 16 may be developed. The first component 110 may be more rigid to provide a structural support, while a second component 120 may be more flexible to allow the "C" shaped cross-section to open. The third component 130 may be absorbent or provide some other beneficial characteristic.

In addition to bonded fiber components, the present invention also discloses integrally forming multi-component structures with non-fibrous components integrally formed therein.

For example, FIG. 4 illustrates an integrally formed three dimensional bonded fiber structure according to a particular embodiment of the invention that is formed with a void 160 within the first component structure 110. This void 160 may be optionally bounded by an impermeable membrane 150 that prevents fluids passed through the first component structure 110 from entering the void 160. Alternatively, the membrane may be permeable to some degree, thereby allowing fluid or vapor to pass through the membrane at a designed, or known, rate. Structures may be formed with multiple voids, if desired. FIG. 5 illustrates an integrally formed three dimensional bonded fiber structure in which the outermost component 120 is bounded by an impermeable membrane 150 that prevents fluid passed through the bicomponent structure 110, 120 from escaping outward. Again, the membrane may alternatively be permeable to some degree, thereby allowing fluid or vapor to pass through the membrane at a designed, or known, rate.

An interface may exist between the two or more components. At the interface, a portion of the fibers from one component may be bonded to fibers of at least one other component. The degree of fiber intermingling between components may be dependent upon the manufacturing process used to manufacture the overall integrally formed bonded fiber multi-component structure. Good bonding over the interface may be achieved when the surface contact between components is maximized, and/or the number of interfacial voids is minimized.

Multi-component structures with particular bonded fiber components may be tailored to specific applications. For example, some fiber types may provide a surface energy that would facilitate wicking of a fluid. Other fiber types may provide bonding advantages. An integrally formed structure of combined fibers may be beneficial in an ink cartridge. A hydrophobic layer could be used to keep ink away from air vents (preventing leakage) and also keep ink out of unproductive corners of a reservoir. As discussed earlier, a particular anisotropic structure may be beneficial in an air deodorizer. For example, an exterior component may be an air permeable three dimensional bonded fiber component and an interior component may be paper impregnated with activated carbon. The exterior three dimensional bonded fiber component may provide support for the interior component, while the interior component may provide the air deodorizer functionality.

Figure 17B:
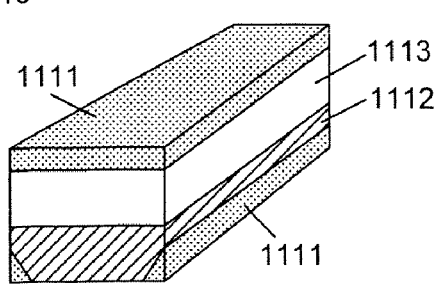
FIG. 17B is an isometric view of an ink jet reservoir, made from a bonded fiber structure, in accordance with some embodiments of the invention.
Figure 17A:
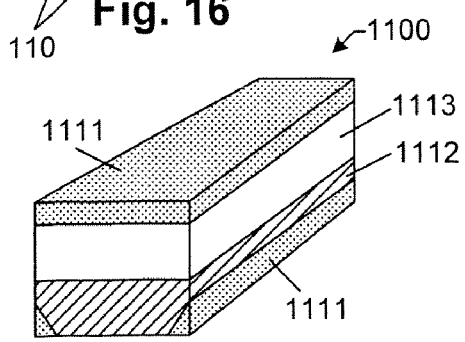
FIG. 17A is an isometric view of an ink jet cartridge, in accordance with some embodiments of the invention.

With reference to FIGS. 17A and 17B, integrally formed multi-component structures wherein the components are three dimensional bonded fiber components, may be used as ink jet reservoirs in printer cartridges. A cartridge 1100 may be comprised of an exterior casing 1105 and a three dimensional bonded fiber reservoir 1110, located inside the exterior casing 1105. The ink jet cartridge 1100 may also include an air vent 1115 and an outlet 1120 that may convey ink to a print head.

The three dimensional bonded fiber reservoir 1110 may be comprised of a plurality of components. The components may be identical, or, as depicted in FIG. 17B, the components may be different or have different properties. The bonded fiber reservoir 1110 may be comprised of components with differing characteristics located in different sections of the reservoir 1110. For example, the ink reservoir 1110 depicted in FIG. 17B may be comprised of three components, 1111, 1112, 1113. The first component 1111 may have hydrophobic or oleophobic properties in order to repel a high surface tension (e.g. water-based) ink or a low surface tension (e.g. oil or alcohol-based) ink away from the air vent 1115, and thus reduce leaking. Similarly, a hydrophobic or oleophobic component 1111 may be used near the corners of the bonded fiber ink reservoir 1110 in order to prevent ink from being trapped there.

A second component 1112 may be hydrophilic or oleophilic. This second component 1112 may attract and hold high surface tension (e.g. water-based) inks or low surface tension (e.g. oil-based or alcohol-based) inks. This second component 1112 may be used in the bonded fiber ink reservoir 1110 to attract the ink through a higher capillary pressure. Finally, a third component 1113 may be included in the three dimensional bonded fiber ink reservoir 1110. The third component 1113 may offer other characteristics beneficial to an ink reservoir, such as but not limited to, high surface energy or high density.

Although multiple components having different materials and different properties have been discussed, it is fully contemplated that the difference between components may be more subtle, such as variations in porosity or fiber orientation of otherwise similar materials. Alternatively, component differences may be limited to distinct levels of porosity. Since porosity affects capillary strength, altering the porosity level of components may serve to draw fluids from one component to another.

Similarly, altering fiber orientation of a bonded fiber structure has been demonstrated to alter fluid flow. Fluid tends to flow along the length of aligned or partially aligned fibers. Accordingly, by altering the direction or degree of alignment of fibers within a bonded fiber component, fluid flow may be manipulated. Fiber orientation may be varied between fiber components or even within a single fiber component. By altering fiber orientation or alignment, directional fluid transfer (i.e., wicking) may be achieved. In addition, fiber orientation may be varied between a first component that has a high degree of alignment (anisotropic) and a second component that has a lower degree of alignment (more isotropic).

Figure 18A:
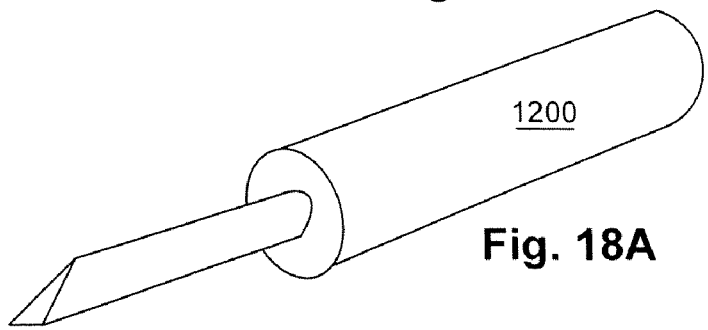
FIG. 18A is an isometric view of a writing device, in accordance with some embodiments of the invention.
Figure 18B:
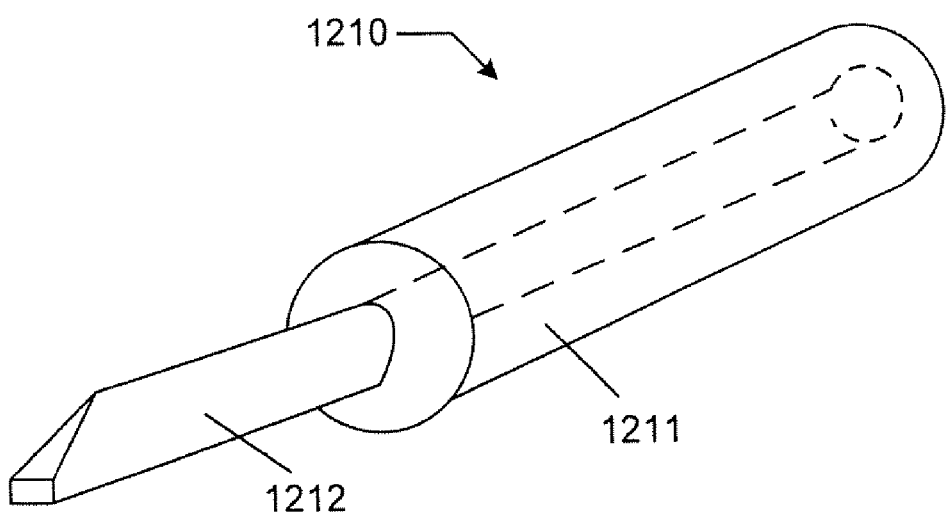
FIG. 18B is an isometric view of a wick/nib combination, made from a bonded fiber structure, in accordance with some embodiments of the invention.

With reference to FIGS. 18A and 18B, integrally formed three dimensional bonded fiber structures according to an embodiment of the invention may also be used as wicks or nibs in writing instruments. FIG. 18A depicts a writing instrument 1200 in accordance with a particular embodiment of the invention. FIG. 18B illustrates a wick and nib 1210 in accordance with a particular embodiment of the invention.

As shown in FIG. 18B, the wick and nib 1210 may be formed of two or more components 1211, 1212. The first component 1211 may possess superior ink holding characteristics, and may thus be positioned in the reservoir section of the writing instrument 1200. The second component 1212 may exhibit superior structural, wicking, and ink release characteristics, and may therefore be positioned in the nib section, or writing section of the writing instrument 1200. The reservoir and nib may be integrally formed. The nib may be further processed, for example chiseled into its final shape suitable for use in a writing instrument. Alternatively, a separate nib piece may be mechanically inserted into the formed reservoir and nib combination.

Figure 19B:
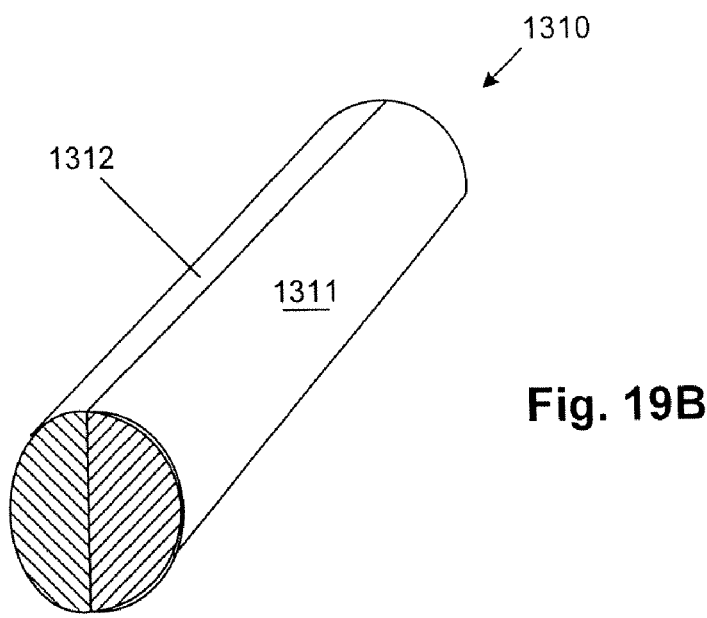
FIG. 19B is an isometric view of a two component air-freshener wick, made from a bonded fiber structure, in accordance with some embodiments of the invention.
Figure 19A:
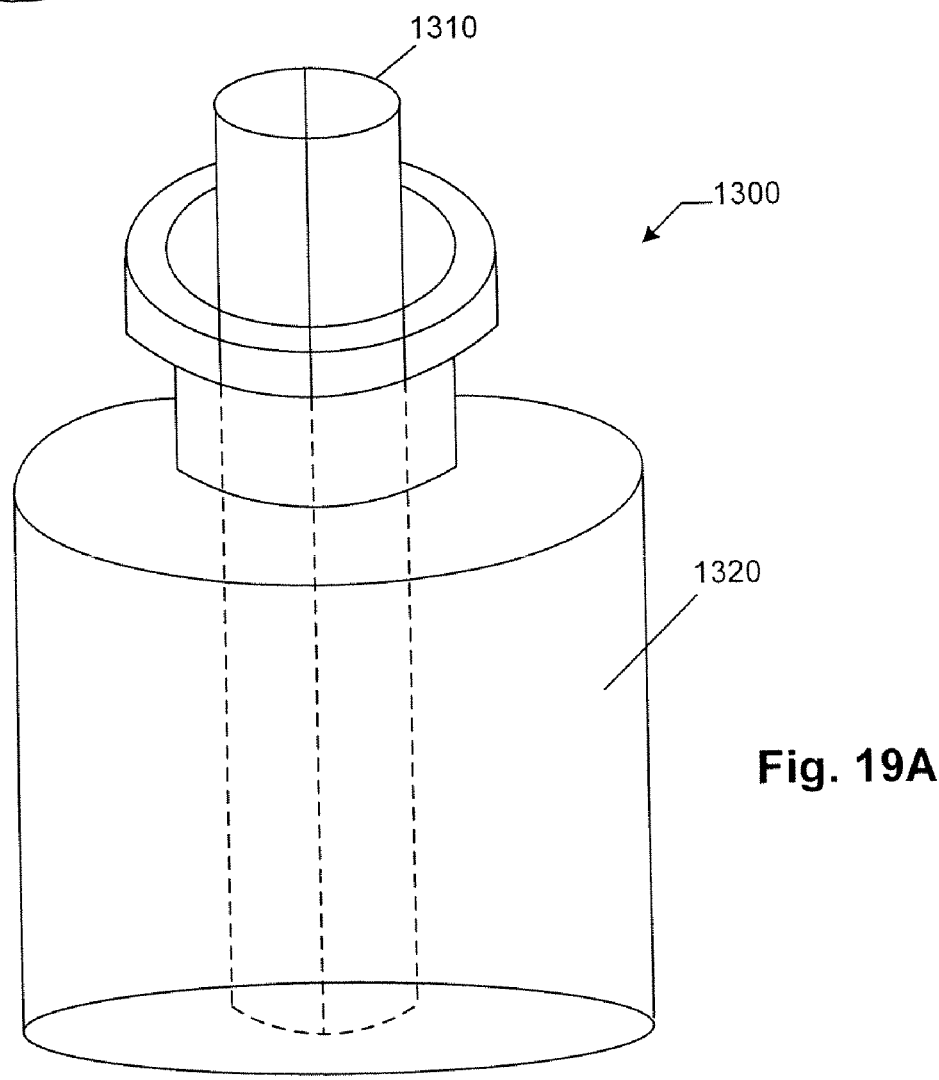
FIG. 19A is an isometric view of an air freshener device, in accordance with some embodiments of the invention.

With reference to FIGS. 19A and 19B, integrally formed three dimensional multi-component bonded fiber structures according to the present invention may also be used in air fresheners. An air freshener 1300 is illustrated in FIG. 19A. The air freshener 1300 may be comprised of a bonded fiber wick 1310 and a reservoir 1320, used to hold fragrant liquids. The reservoir 1320 is typically an open (free liquid) air freshener reservoir. The air freshener 1300 depicted in FIG. 19A may use two fragrant liquids. These may be immiscible liquids where one has as a higher surface tension (e.g. water-based) liquid and the other has a lower surface tension (e.g. oil-based or alcohol-based). As illustrated, the wick 1310 is comprised of two integrally formed, bonded fiber components, 1311, 1312, although it is fully contemplated that it may be comprised of any number of components. The first component 1311 may be designed to wick the higher surface tension fluids (e.g. water-based fluids) while the second component 1312 may be designed to wick the lower surface tension fluids (e.g. oil-based or alcohol-based fluids). The two components 1311, 1312 may be designed to accommodate equal rates of wicking and evaporation for each fragrant liquid.

The air freshener wick 1310 may also be designed with several aesthetic considerations in mind. For example, the color of each bonded fiber component 1311, 1312 may be selected to illustrate to a user or observer that both liquids are being used equally. Similarly, if the color of one liquid is unappealing, the bonded fiber component that wicks that particular liquid may be nested within another component to effectively hide the unappealing liquid.

Figure 20:
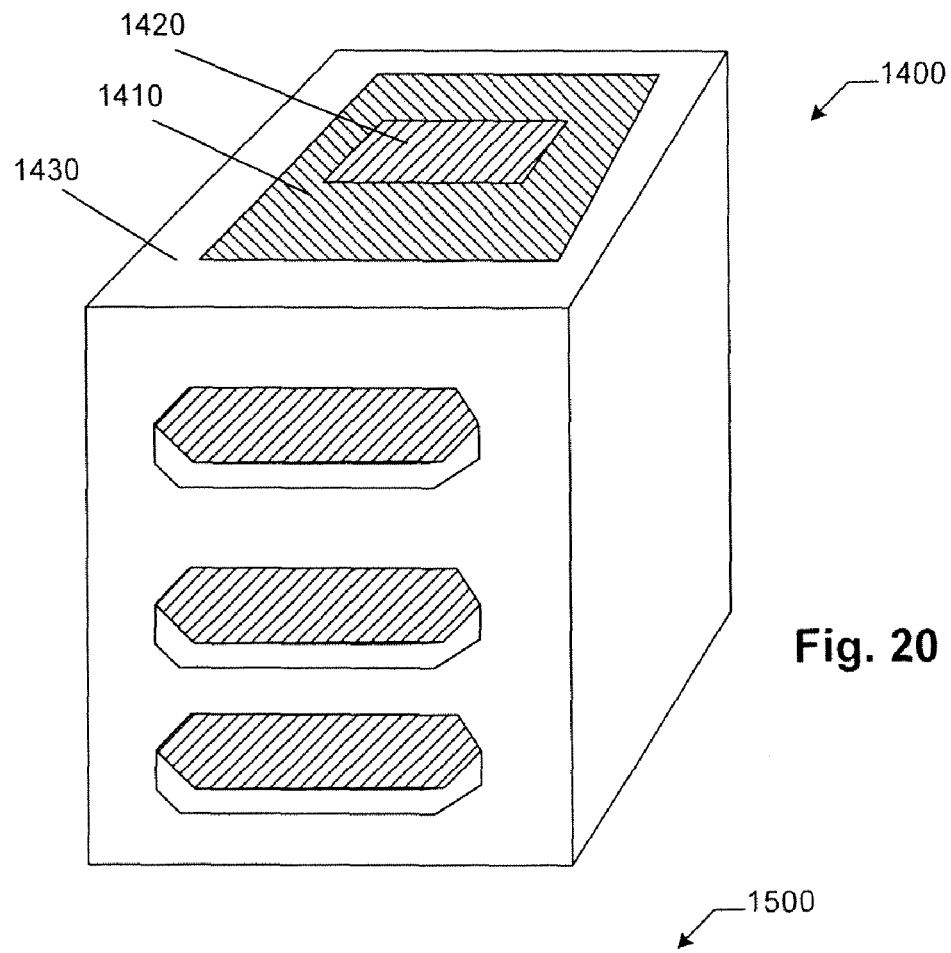
FIG. 20 is an isometric view of an air deodorizer, in accordance with some embodiments of the invention.

With reference to FIG. 20, an air deodorizer 1400 will now be discussed. The air deodorizer 1400 may be integrally formed from two or more components. A first component 1410 may be a three dimensional bonded fiber structure and it may enclose a second component 1420. The second component 1420 may also be a three dimensional bonded fiber structure integrally formed with the first component 1410. The second component 1420 may be nested within the first component 1410, and may provide for air deodorization, for example, through the use of paper impregnated with activated carbon. The first component 1410 may be air permeable, may be an aesthetically pleasing color, and may provide structural support for the second component 1420. Both the first and the second component may be disposed within a casing 1430 or other such enclosure.

Figure 21:
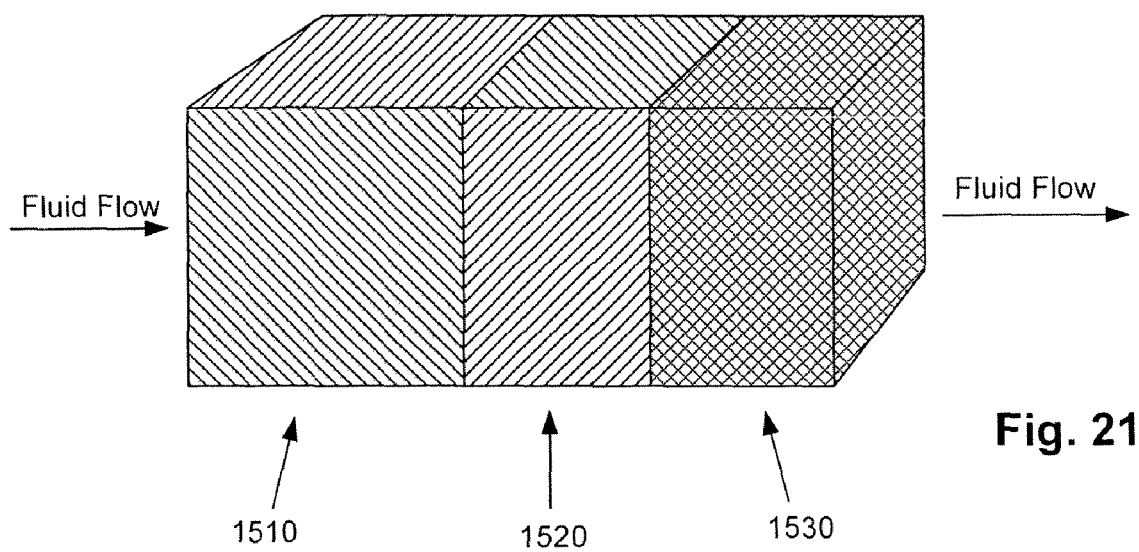
FIG. 21 is an isometric view of a depth filter in accordance with some embodiments of the invention.

With reference to FIG. 21, two or more components may be used to form a depth filter 1500. The depth filter 1500 may be comprised of a first component 1510 and a second component 1520. The first component material may differ from the second component material such that as a fluid flows through the depth filter 1500 various levels of filtering are achieved. In other words, the first component 1510 may be of a certain porosity (e.g. have a larger pore size), while the second component 1520 may be less porous (e.g. have a smaller pore size). A third component 1530 may be used that may be even less porous than the second component 1520 (e.g. have an even smaller pore size), and so on. Multiple components may be used in order to produce a gradient in filtering abilities, thereby slowing the rise in pressure drop and increasing filter useful life. A filter gradient may also be achieved through variation of fiber diameter. A first component 1510 may have a particular fiber diameter, while a second component 1520 may have a smaller fiber diameter, and a third component 1530 may have an even smaller fiber diameter. This change in fiber diameter may also thereby create a gradient in filtering abilities, even if other parameters such as density are held constant.

It is contemplated that multiple other products can be made from such integrally formed multi-component structures with at least one three dimensional bonded fiber component. The application of such multi-component structures is not limited to ink reservoirs, wicks and nibs, air freshener wicks, air deodorizers, or depth filters as described above. These structures may also be used in medical equipment and diagnostic devices, as filter elements in a multitude of applications, and as absorption pads for diapers or incontinence pads. Other applications could be specialty filters, where the different layers would present different filtration characteristics.

Fibers may be selected based upon the desired characteristics of the final product. Fiber qualities which may be varied include: the overall fiber material for mono-component fibers, the fiber core and sheath material for bicomponent fibers, the fiber diameter, the fiber length, the fiber orientation, finishes on the fiber (e.g. hydrophilic, hydrophobic), the crimp level of the fiber, or any particulate loading of the fibers.

The selection of these fibers and fiber characteristics may impact the manufacturing process. For example, if staple fibers are used, the first stage of the manufacturing is generally opening, or isotropically distributing, the staple. Following opening, the fibers are distributed into a web. The web production may occur in at least two ways: carding or air-laying. Carding fibers is combing the fibers so that the fibers generally lay in the same orientation. Air-laying fibers generally results in the fibers having an entirely isotropic (or random) orientation. If the fibers are carded, the desired length is generally between 20 mm and 50 mm. However, if the fibers are air-laid, the desired length is generally between 4 mm to 30 mm. In a filament or continuous fiber process, the fibers are not cut into staple fibers, but may be used in a continuous fashion, utilizing either creeled filaments, filament processed into crimped tows, or as continuous melt-blown or spun-bond webs.

It will be understood that different components of the integrally formed multi-component structures made from a plurality of three dimensional bonded fiber structure may have the same fiber material, but in a different form. For example, one component may have long, hot air bonded staple fibers, while another component may have continuous fibers or short, air-laid staple fibers of the same material. The different components may also have differences as simple as porosity differences (for example, a highly porous, low density layer and a low porosity, high density layer). In this case, the layer with the small pores will have a higher capillary strength that that with the larger pores.

Once the staple fibers are arranged, they may undergo another process to form a sustainable web. Forming of the web may occur through a variety of processes. The fibers may be heated, such that initial point-to-point bonding occurs enough to sustain a web. The fibers may be passed through a through-air bonding oven to form a substantially self-sustaining web. Instead, the fibers may also undergo needle-punching, where multiple needles push through the fibers, causing the fibers to be tangled in such a manner as to cause a sustainable web. The fibers may also be hydro-entangled. The sustainable webs may then be rolled up or otherwise gathered and prepared for the next process.

Integrally formed three dimensional bonded fiber structures may be made by several manufacturing processes. An example of a process that can be used to make the composite structures of the invention is a pneumatic forming process, such as that disclosed in U.S. Pat. Nos. 3,533,416, 3,599,646 3,637,447 and 3,703,429, each of which is incorporated herein by reference in its entirety. The process utilizes tows of fibers (such as cellulose acetate or nylon), which, when treated with a plasticizer, may be impinged in a forming die with air pressure and then treated with steam to form a porous, 3 dimensional, self sustaining, bonded fiber structure. The process can be modified to produce the composite structures of the invention by using a forming die having a plurality of zones. Using this die, tows with different fiber sizes, cross sections or feed rates can be used to form composite materials with configurations similar to those of FIGS. 1-11.

Alternatively, multi-component structures made from different fibrous components may be formed using continuous processing methods similar to those used to produce isotropic fibrous structures. In these methods, one or more of the fibrous components may be formed from fiber feed materials comprising a fiber component formed from a bondable polymer that, upon application of heat (in the form of steam or hot air) will soften and, when in contact with another fiber, bond to that fiber at the contact point. The fibers used in one or more of the fiber components may be, for example, bicomponent sheath/core fibers having a bondable sheath layer.

The fibers used in the forming process may be in the form of bundled individual filaments, tows, roving or lightly bonded non-woven webs or sheets. The fibers may be mechanically crimped or may be structured so that self-crimping may be induced (e.g., by stretching and then relaxing the fibers) during the continuous forming process. The fibers may also be melt blown or formed by a spun bond process.

Figure 22:
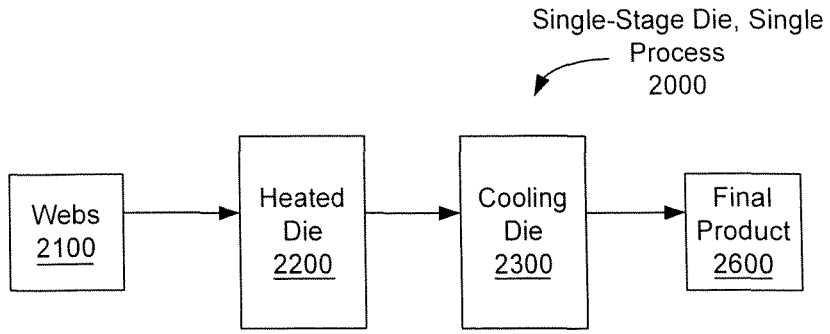
FIG. 22 is a block diagram, graphically illustrating a first method of manufacturing a multi-component structure, with at least one three dimensional bonded fiber component, in accordance with some embodiments of the invention.
Figure 23:
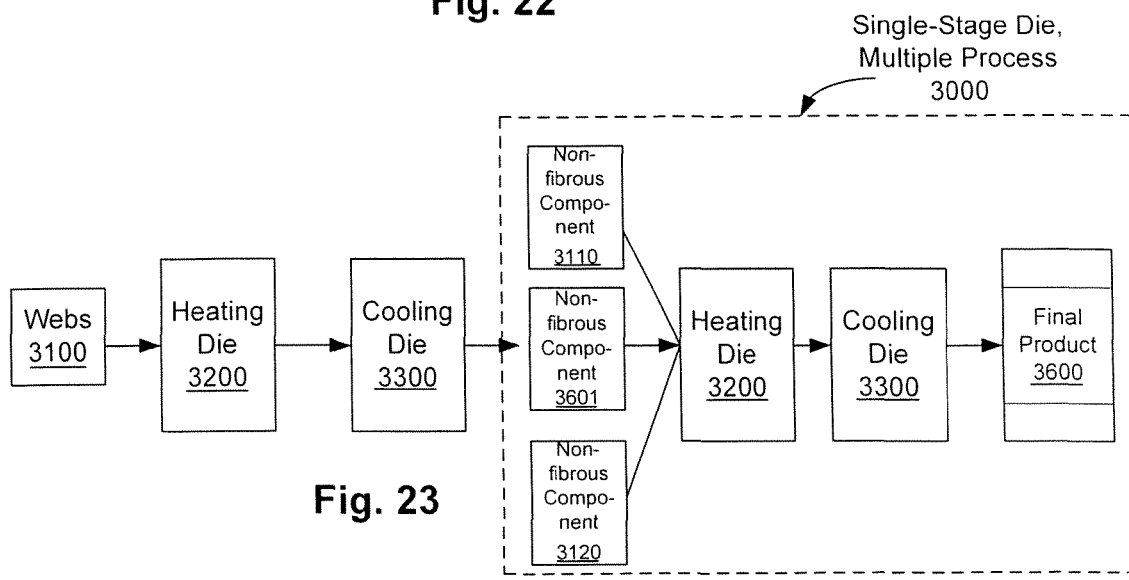
FIG. 23 is a block diagram, graphically illustrating a second method of manufacturing a multi-component structure, with at least one three dimensional bonded fiber component, in accordance with some embodiments of the invention.
Figure 24:
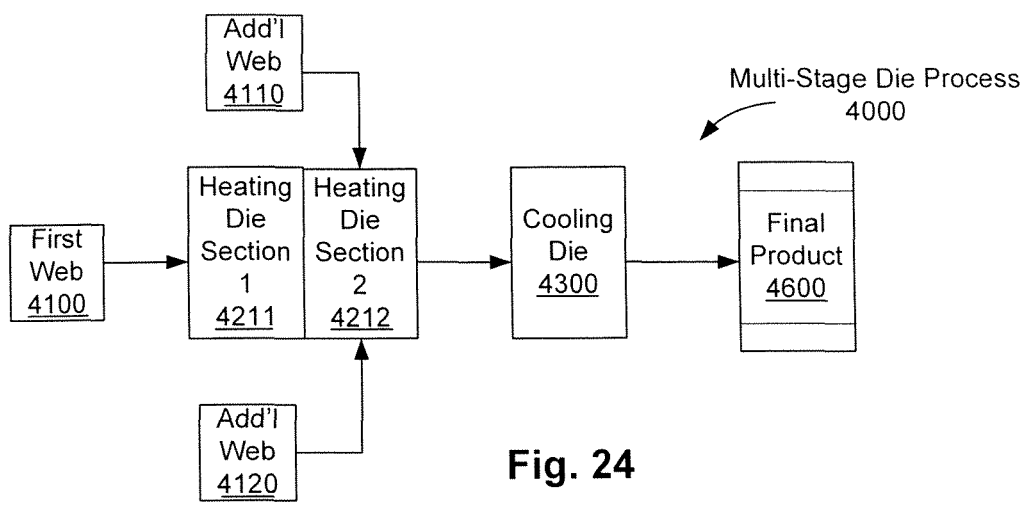
FIG. 24 is a block diagram, graphically illustrating a third method of manufacturing a multi-component structure, with at least one three dimensional bonded fiber component, in accordance with some embodiments of the invention.

With reference to FIGS. 22-24, each process may result in different characteristics of the interface between the two or more components. A single-stage die, single process 2000 may be used, where materials are put into a single-stage die, and undergo one process to form an integrally formed three dimensional bonded fiber structure. A single-stage die, multiple process 3000 may be used, where materials are fed into a single-stage die, undergo a process, and the resultant product and other materials are fed into a second single-stage die and undergo a second process to form an integrally formed three dimensional bonded fiber structure. A multi-stage die process 4000 may also be used, where materials are fed into a multi-stage die and undergo at least one process to form an integrally formed bonded fiber structure.

In order to make a three dimensional bonded fiber structure using the single-stage die, single process 2000, webs 2100 may be fed into a heated die 2200. As illustrated in FIG. 22, once the webs 2100 are fed into the heating die 2200, the heating die 2200 may cause heat to be applied to the webs 2100. In the heating die, the surface (or sheath) of bicomponent fibers soften, and where they come into contact, they begin to stick to one another. If monocomponent fibers are used, a plasticizer may be used to facilitate the monocomponent fibers to bond to themselves at spaced points of contact without losing their fibrous structure. Once the material is fed through the heating die 2200, it may be fed into a cooling die 2300. In the cooling die, the softened fiber surface (either a sheath polymer or the plasticized surface of the fiber) hardens, establishing the bonding of the fibers at points of contact. The final product 2600 is then removed from the cooling die 2300, and if necessary, cut to size.

The discussion above reflects the simplest process for the formation of an isotropic or anisotropic three dimensional bonded fiber structure according to an embodiment of the invention. Variations in the process, including the type of die used and the order of the manufacturing steps may occur, and are discussed below.

With reference to FIG. 23, in some embodiments, the single-stage die, multiple process 3000 may be used. In this process 3000, an additional component may be formed integral to a final product 3600 by repeating the process discussed above. A previously formed component may be formed using any of the processes 2000, 3000, 4000 described herein. The previously formed or a non-fibrous component 3601 may be fed into a heating die 3200 with at least one layer of a newly added fibrous web 3101 in contact with the previously formed or non-fibrous component 3601. The previously formed or non-fibrous component 3601 and the newly added fibrous web 3101 may then be heated in the heating die 3200, and fed into the cooling die 3300. This process may be used to form multilayer constructions of the type depicted in FIG. 1, 2, 3, 4, 5, 9, 11, 14, 16, 18 or 19).

In the second heating die, the surface of the already formed component 3601 may soften, thereby allowing the newly added fibrous web 3101 to bond or adhere to the already formed component 3601. If desired, this process may be repeated multiple times. The final product is then removed from the cooling die 3300, and if necessary, cut to size.

In accordance with some embodiments of the present invention, a multi-stage die process 4000 may be used. With reference to FIG. 24, integrally formed multi-component structures may be manufactured using a single, multi-stage heating die 4210. The multi-stage heating die 4210 may be comprised of two sections, 4211, 4212. The first section 4211 may be sized to heat a first web 4100. This first web 4100 may enter the heating die as described above. The second section 4212 may be sized to heat additional webs 4110, 4120. Downstream of where the first web 4100 enters the multi-stage heating die 4210, additional webs 4110, 4120 may enter the multi-stage heating die 4210 in the second section 4212. All webs 4100, 4110, 4120 may be thereby formed as a single component. This single component may then be fed into a cooling die 4300 and after, if necessary, cut to the desired size.

The manufacture of self-sustaining three-dimensional multi-component structures using both the single-stage heating die 2200 and the multi-stage heating die 4210 can be modified by varying the fiber type used in the webs. For example, each layer of webs fed into the heating dies may or may not be of the same characteristics (e.g., fiber core material, fiber sheath material, fiber length, finishes, loading, density (or basis weight) of the feed web, etc.). Varying these characteristics of the component fibers may accordingly vary the characteristics of the final product.

Substantially isotropic multi-component fibrous structures may be obtained by feeding webs 2100 of the same characteristics into the single-stage heating die 2200 at the same time. Because each of the webs 2100 are heated and cooled simultaneously, the interface that exists between the webs is less discernible and there may be considerable commingling of fibers from each component. When webs made of fibers of the same characteristics are formed into self-sustaining three dimensional fibrous structures in a multi-stage heating die 4210, the interface between webs 4100, 4110, 4120 formed at different die stages may be more discernible.

However, when fibers of the same characteristics are formed integral to an existing component of identical fiber characteristics, the interface between components may be discernible. This interface may be defined a slight change in the density of the finished component at the interface due to a smaller amount of intermingling fibers from each component. In other words, because one portion of the finished multi-component structure was formed and cooled previously, it may not have any loose fibers that may bond with fibers from the incoming component. Therefore, the interface between the components formed at different times may have a slight density difference.

It will be apparent to those skilled in the art that various modifications and variations can be made in the method, manufacture, configuration, and/or use of the present invention without departing from the scope or spirit of the invention.

What is claimed is:

1. An integrally formed multi-component structure comprising a plurality of fluid transmissive components, at least one of which is a three-dimensional bonded fiber fluid transmissive component comprised of a plurality of polymeric fibers bonded to each other at spaced apart contact points, the fibers collectively defining tortuous fluid flow paths, wherein the three dimensional bonded fiber fluid transmissive component has a predetermined cross-sectional shape that is substantially constant along at least one axis of the multi-component structure and wherein each fluid transmissive component has an interface with at least one other fluid transmissive component.

2. The integrally formed multi-component structure of claim 1, wherein the three-dimensional bonded fiber fluid transmissive component has a first set of fluid flow characteristics and another fluid transmissive component of the multi-component structure has a second set of fluid flow characteristics that is different from the first set of fluid flow characteristics.

3. The integrally formed multi-component structure of claim 1, wherein the plurality of fluid transmissive components includes a plurality of three-dimensional bonded fiber fluid transmissive components.

4. The integrally formed multi-component structure of claim 3, wherein at least a portion of the fibers of each three-dimensional bonded fiber fluid transmissive component is bonded to fibers of at least one other three-dimensional bonded fiber fluid transmissive component across the interface at spaced apart contact points.

5. The integrally formed multi-component structure of claim 3, wherein the plurality of three-dimensional bonded fiber fluid transmissive components includes a first three-dimensional bonded fiber fluid transmissive component having a first set of fluid flow characteristics and a second three-dimensional bonded fiber fluid transmissive component having a second set of fluid flow characteristics that is different from the first set of fluid flow characteristics.

6. The integrally formed multi-component structure of claim 3, wherein the plurality of three-dimensional bonded fiber fluid transmissive components includes a first three-dimensional bonded fiber fluid transmissive component having a first set of fiber characteristics and a second three-dimensional bonded fiber fluid transmissive component having a second set of fiber characteristics that is different from the first set of fiber characteristics.

7. The integrally formed multi-component structure of claim 6, wherein the difference between the first set of fiber characteristics and the second set of fiber characteristics includes a difference in one or more properties selected from the group consisting of: fiber compositions, fiber surface energies, fiber geometries, fiber cross-sections, fiber color, and fiber coatings.

8. The integrally formed multi-component structure of claim 6, wherein the first three-dimensional bonded fiber fluid transmissive component has an interface with the second three-dimensional bonded fiber fluid transmissive component and the first and second sets of fiber characteristics are selected to provide a desired flow behavior across the interface between the first and second three-dimensional bonded fiber fluid transmissive components.

9. The integrally formed multi-component structure of claim 2, wherein the at least one three-dimensional bonded fiber fluid transmissive component has an interface with another fluid transmissive component of the multi-component structure, and the first and second set of fluid flow characteristics are selected to provide a desired flow behavior across the interface of the at least one three-dimensional bonded fiber fluid transmissive component and another fluid transmissive component of the multi-component structure.

10. The integrally formed multi-component structure of claim 1, wherein the predetermined cross-sectional shape of the at least one three-dimensional bonded fiber fluid transmissive component is asymmetrically arranged with respect to the multi-component structure axis.

11. The integrally formed multi-component structure of claim 1, wherein the multi-component structure cross-section is asymmetric with respect to the multi-component structure axis.

12. The integrally formed multi-component structure of claim 1, wherein the predetermined shape of the at least one three-dimensional bonded fiber component is axisymmetric with respect to the multi-component structure axis.

13. The integrally formed multi-component structure of claim 1, wherein the predetermined cross-sectional shape of each of the at least one three-dimensional bonded fiber fluid transmissive component is axisymmetric with respect to the multi-component structure axis.

14. An integrally formed multi-component structure comprising a plurality of three-dimensional bonded fiber fluid transmissive components, each comprising a plurality of polymeric fibers bonded to each other at spaced apart contact points, the fibers collectively defining tortuous fluid flow paths, wherein a first three-dimensional bonded fiber fluid transmissive component has a first predetermined cross-sectional shape that is substantially constant along at least one axis of the multi-component structure and a first set of fluid flow characteristics and a second three-dimensional bonded fiber fluid transmissive component has a second predetermined cross-sectional shape that is substantially constant along at least one axis of the multi-component structure and a second set of fluid flow characteristics that is different from the first set of fluid flow characteristics, and wherein the first three-dimensional bonded fiber fluid transmissive component has an interface with the second three-dimensional bonded fiber fluid transmissive component.

15. The integrally formed multi-component structure of claim 14, wherein at least a portion of the fibers of the first three-dimensional bonded fiber fluid transmissive component is bonded to fibers of the second three-dimensional bonded fiber fluid transmissive component across the interface at spaced apart contact points.

16. The integrally formed multi-component structure of claim 14, wherein the first three-dimensional bonded fiber fluid transmissive component has a first set of fiber characteristics and the second three-dimensional bonded fiber fluid transmissive component has a second set of fiber characteristics that is different from the first set of fiber characteristics.

17. The integrally formed multi-component structure of claim 16, wherein the difference between the first set of fiber characteristics and the second set of fiber characteristics includes a difference in one or more properties selected from the group consisting of: fiber compositions, fiber surface energies, fiber geometries, fiber cross-sections, fiber color, and fiber coatings.

18. The integrally formed multi-component structure of claim 16, wherein the first and second sets of fiber characteristics are selected to provide a desired flow behavior across the interface between the first and second three-dimensional bonded fiber fluid transmissive components.

19. The integrally formed multi-component structure of claim 14, wherein the cross-sectional shape of each three-dimensional bonded fiber fluid transmissive component is axisymmetric with respect to the axis of the multi-component structure.

20. A method of forming an ink jet printer cartridge, the method comprising:
providing an exterior case defining a reservoir cavity;
providing an integrally formed multi-component structure comprising a plurality of fluid transmissive components, at least one of which is a three-dimensional bonded fiber fluid transmissive component comprised of a plurality of polymeric fibers bonded to each other at spaced apart contact points, the fibers collectively defining tortuous fluid flow paths, the three dimensional bonded fiber fluid transmissive component having a predetermined cross-sectional shape that is substantially constant along at least one axis of the multi-component structure, and each fluid transmissive component having an interface with at least one other fluid transmissive component; and
disposing the multi-component structure within the reservoir cavity to form the ink jet printer cartridge.

21. A method of forming an ink jet printer cartridge according to claim 20 further comprising:
introducing ink into the reservoir cavity, at least a portion of the ink being drawn into and held within the at least one three dimensional bonded fiber fluid transmissive component of the multi-component structure.

22. A method of forming an ink jet printer cartridge according to claim 20, wherein the plurality of fluid transmissive components includes a plurality of three-dimensional bonded fiber fluid transmissive components.

23. A method of forming an ink jet printer cartridge according to claim 22, wherein at least a portion of the fibers of each three-dimensional bonded fiber fluid transmissive component is bonded to fibers of at least one other three-dimensional bonded fiber fluid transmissive component across the interface at spaced apart contact points.

24. A method of forming an ink jet printer cartridge according to claim 22, wherein the plurality of three-dimensional bonded fiber fluid transmissive components includes a first three-dimensional bonded fiber fluid transmissive component having a first set of fluid flow characteristics and a second three-dimensional bonded fiber fluid transmissive component having a second set of fluid flow characteristics that is different from the first set of fluid flow characteristics.

25. A method of forming an air freshener, the method comprising:
providing an exterior case defining a reservoir cavity;
providing a wick comprising a multi-component structure comprising a plurality of fluid transmissive components, at least one of which is a three-dimensional bonded fiber fluid transmissive component comprised of a plurality of polymeric fibers bonded to each other at spaced apart contact points, the fibers collectively defining tortuous fluid flow paths, the three dimensional bonded fiber fluid transmissive component having a predetermined cross-sectional shape that is substantially constant along at least one axis of the multi-component structure, and each fluid transmissive component having an interface with at least one other fluid transmissive component, the wick having first and second wick ends; and
disposing at least a portion of the wick within the reservoir cavity so that the first wick end would be in fluid communication with liquid introduced into the reservoir cavity.

26. A method of forming an air freshener according to claim 25 further comprising:
introducing liquid into the reservoir cavity so that the first wick end is in fluid communication with the liquid and so that at least a portion of the liquid is drawn into the at least one three dimensional bonded fiber fluid transmissive component of the multi-component structure and is drawn toward the second wick end.

27. A method of forming an air freshener according to claim 25, wherein the plurality of fluid transmissive components includes a plurality of three-dimensional bonded fiber fluid transmissive components.

28. A method of forming an air freshener according to claim 27, wherein at least a portion of the fibers of each three-dimensional bonded fiber fluid transmissive component is bonded to the fibers of at least one other three-dimensional bonded fiber fluid transmissive component across the interface at spaced apart contact points.

29. A method of forming an air freshener according to claim 27, wherein the plurality of three-dimensional bonded fiber fluid transmissive components includes a first three-dimensional bonded fiber fluid transmissive component having a first set of fluid flow characteristics and a second three-dimensional bonded fiber fluid transmissive component having a second set of fluid flow characteristics that is different from the first set of fluid flow characteristics.

30. The integrally formed multi-component structure of claim 1, wherein the predetermined cross-sectional shape is selected from a set consisting of a rectangle, a circle, and a semicircle.

31. The integrally formed multi-component structure of claim 1, wherein each of the plurality of fluid transmissive components has a predetermined cross-sectional component shape that is substantially constant along the at least one of the at least one axis of the multi-component structure.

32. The integrally formed multi-component structure of claim 31, wherein each predetermined cross-sectional component shape is selected from a set consisting of a rectangle, a circle, and a semicircle.

33. The integrally formed multi-component structure of claim 14, wherein the first and second predetermined cross-sectional shapes are each selected from a set consisting of a rectangle, a circle, and a semicircle.

34. The integrally formed multi-component structure of claim 14, wherein each of the plurality of three-dimensional bonded fiber fluid transmissive components has a predetermined cross-sectional component shape that is substantially constant along the at least one of the at least one axis of the multi-component structure.

35. The integrally formed multi-component structure of claim 34, wherein each predetermined cross-sectional component shape is selected from a set consisting of a rectangle, a circle, and a semicircle.

36. The integrally formed multi-component structure of claim 20, wherein the predetermined cross-sectional shape is selected from a set consisting of a rectangle, a circle, and a semicircle.

37. The integrally formed multi-component structure of claim 20, wherein each of the plurality of fluid transmissive components has a predetermined cross-sectional component shape that is substantially constant along the at least one of the at least one axis of the multi-component structure.

38. The integrally formed multi-component structure of claim 37, wherein each predetermined cross-sectional component shape is selected from a set consisting of a rectangle, a circle, and a semicircle.

39. The integrally formed multi-component structure of claim 25, wherein the predetermined cross-sectional shape is selected from a set consisting of a rectangle, a circle, and a semicircle.

40. The integrally formed multi-component structure of claim 25, wherein each of the plurality of fluid transmissive components has a predetermined cross-sectional component shape that is substantially constant along the at least one of the at least one axis of the multi-component structure.

41. The integrally formed multi-component structure of claim 40, wherein each predetermined cross-sectional component shape is selected from a set consisting of a rectangle, a circle, and a semicircle.

* * * * *